US012708715B2

(12) United States Patent
Loughnane et al.

(10) Patent No.: US 12,708,715 B2
(45) Date of Patent: Aug. 18, 2026

(54) MEDICATION DELIVERY DEVICE WITH SYRINGE SENSING SYSTEM

(71) Applicant: Eli Lilly and Company, Indianapolis, IN (US)

(72) Inventors: Christopher Paul Loughnane, Brookline, MA (US); Gaurav Rohatgi, Waltham, MA (US); Stephen Louis Snyder, Bedford, MA (US)

(73) Assignee: Eli Lilly and Company, Indianapolis, IN (US)

( * ) Notice: Subject to any disclaimer, the term of this patent is extended or adjusted under 35 U.S.C. 154(b) by 815 days.

(21) Appl. No.: 16/767,636

(22) PCT Filed: Dec. 6, 2018

(86) PCT No.: PCT/US2018/064177
§ 371 (c)(1),
(2) Date: May 28, 2020

(87) PCT Pub. No.: WO2019/118261
PCT Pub. Date: Jun. 20, 2019

(65) Prior Publication Data

US 2020/0368441 A1 Nov. 26, 2020

Related U.S. Application Data

(60) Provisional application No. 62/599,029, filed on Dec. 15, 2017.

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/31583* (2013.01);
(Continued)

(58) Field of Classification Search
CPC .............. A61M 5/3157; A61M 5/2033; A61M 5/31583; A61M 5/3234; A61M 2005/206;
(Continued)

(56) References Cited

U.S. PATENT DOCUMENTS 4,552,055 A 11/1985 Foxwell
6,491,657 B2 12/2002 Rowe et al.
(Continued)

FOREIGN PATENT DOCUMENTS

CN 107106785 A 8/2017
EP 3199188 8/2017
(Continued)

OTHER PUBLICATIONS

Patent Cooperation Treaty International Search Report pertaining to International Application No. PCT/US2018/064177; International Filing Date: Dec. 6, 2018; Date of Mailing: May 29, 2019.
(Continued)

*Primary Examiner* — Kami A Bosworth
*Assistant Examiner* — Avery Smale
(74) *Attorney, Agent, or Firm* — Arthur Shum

(57) ABSTRACT

A medication delivery device including a drive mechanism, a retraction mechanism and a sensing system. A medication container is movable relative to the medication delivery device between storage and delivery positions. The drive mechanism drives a plunger in a translational movement to move the medication container from the storage position to the delivery position and to dispense medication from the medication container in a dispensing event. The retraction mechanism includes a rotary member that rotates during a retraction movement of the retraction mechanism. The sensing system includes a first sensor to detect operational status and a second sensor to sense rotational movement of the rotary member. A controller is configured to detect initiation
(Continued)

of the dispensing event based on signals generated by the first sensor and detect completion of the dispensing event and/or completion of the retraction movement based on signals generated by the second sensor.

6 Claims, 10 Drawing Sheets

(52) U.S. Cl.
CPC ..... *A61M 5/3234* (2013.01); *A61M 2005/206* (2013.01); *A61M 2005/2073* (2013.01); *A61M 2205/3306* (2013.01); *A61M 2205/3327* (2013.01)

(58) Field of Classification Search
CPC .. A61M 2005/2073; A61M 2205/3306; A61M 2205/3327; A61M 2005/3125; A61M 5/20; A61M 2005/3126; A61M 2205/35; A61M 5/31571; A61M 5/31566; A61M 2205/3317; A61M 2205/332
See application file for complete search history.

(56) References Cited

U.S. PATENT DOCUMENTS

| | | | |
|---|---|---|---|
| 6,547,755 | B1 | 4/2003 | Lippe et al. |
| 6,793,633 | B2 | 9/2004 | Douglas et al. |
| 7,628,780 | B2 | 12/2009 | Bonner et al. |
| 7,927,288 | B2 | 4/2011 | Gianchandani et al. |
| 8,197,449 | B2 | 6/2012 | Nielsen et al. |
| 8,734,394 | B2 | 5/2014 | Adams et al. |
| 9,101,723 | B2 | 8/2015 | Larsen |
| 9,220,837 | B2 | 12/2015 | Pesach et al. |
| 9,561,332 | B2 | 2/2017 | Butler et al. |
| 9,789,260 | B1 | 10/2017 | Binier |
| 9,849,252 | B2 | 12/2017 | Armes |
| 9,872,633 | B2 | 1/2018 | Limaye et al. |
| 11,197,963 | B2 * | 12/2021 | Helmer .................. A61M 5/20 |
| 2009/0030285 | A1 | 1/2009 | Andersen |
| 2014/0194825 | A1 | 7/2014 | Nielsen et al. |
| 2014/0236084 | A1 * | 8/2014 | Adams ................ A61M 5/2033 604/135 |
| 2015/0250413 | A1 | 9/2015 | Redwood et al. |
| 2015/0290396 | A1 | 10/2015 | Nagar et al. |
| 2016/0129182 | A1 | 5/2016 | Schuster et al. |
| 2016/0136353 | A1 | 5/2016 | Adams |
| 2016/0193415 | A1 | 7/2016 | Cowe |
| 2016/0256639 | A1 | 9/2016 | Van Sickle et al. |
| 2016/0259913 | A1 * | 9/2016 | Yu ..................... A61M 5/31511 |
| 2016/0263327 | A1 | 9/2016 | Radmer et al. |
| 2016/0296699 | A1 * | 10/2016 | Cabiri .................... A61M 5/20 |
| 2017/0189625 | A1 | 7/2017 | Cirillo et al. |
| 2017/0245943 | A1 | 8/2017 | Foster et al. |
| 2017/0257436 | A1 | 9/2017 | Starr et al. |
| 2018/0014787 | A1 | 1/2018 | Ganton et al. |

FOREIGN PATENT DOCUMENTS

| | | | |
|---|---|---|---|
| EP | 3381493 | | 10/2018 |
| JP | 2012519028 | A | 8/2012 |
| JP | 2017525473 | A | 9/2017 |
| WO | 20060134153 | | 12/2006 |
| WO | 2010019456 | | 2/2010 |
| WO | 2010098927 | A1 | 9/2010 |
| WO | 20110109205 | | 9/2011 |
| WO | 20130034716 | | 3/2013 |
| WO | 20140111343 | | 7/2014 |
| WO | 2015187797 | | 12/2015 |
| WO | 2016026679 | A1 | 2/2016 |
| WO | 2016113348 | | 7/2016 |
| WO | 20160115372 | | 7/2016 |
| WO | 20160140853 | | 9/2016 |
| WO | 2017071927 | | 5/2017 |
| WO | 2017108272 | | 6/2017 |
| WO | 2017114908 | | 7/2017 |
| WO | 2017129314 | | 8/2017 |
| WO | 2017201185 | A1 | 11/2017 |
| WO | 2017215887 | | 12/2017 |
| WO | 20180085952 | | 5/2018 |
| WO | 2018178888 | | 10/2018 |
| WO | 20180200452 | | 11/2018 |

OTHER PUBLICATIONS

Patent Cooperation Treaty Written Opinion of the International Searching Authority Report pertaining to International Application No. PCT/US2018/064177; International Filing Date: Dec. 6, 2018; Date of Mailing: May 29, 2019.

Magill, John C., et al., "A Novel Actuator for Simulation of Epidural Anesthesia and Other Needle Insertion Procedures," *Simul Healthc.* Jun. 2010; 5(3); pp. 179-184.

* cited by examiner 82
74
76
72
70
80
80
114
112
28

106
108
96
98
104
110
92
94
100
102
28

116
72
99
52
114
74
70
76
80
112
80
28

MEDICATION DELIVERY DEVICE WITH SYRINGE SENSING SYSTEM

BACKGROUND

The present disclosure pertains to medication delivery devices, and, in particular, to a sensing system in a medication delivery device.

Medication delivery devices that include a syringe are widely employed by medical professionals and patients who self-medicate. Patients suffering from a number of different diseases frequently must inject themselves with medication and a variety of devices have been developed to facilitate such self-medication. Such devices typically include a syringe having a syringe barrel that holds a medication and a drive system to expel the medication from the syringe barrel through a needle bore into the patient. The device may be an automatic injection device, which includes mechanisms to perform some of the steps of the injection process automatically, rendering it more convenient for a patient to self-medicate. Due to the construction and design of such devices, it is difficult to determine the operational status of the device. While a number of functional medication delivery devices are currently available, improvements in such medication delivery devices remain desirable.

SUMMARY

In accordance with an embodiment of the present disclosure, a medication delivery device includes a housing, a medication container, a drive mechanism, a retraction mechanism, and a sensing system. The medication container includes a container body to hold a medication and a slidable piston operably coupled with the container body. The slidable piston is movable relative to the container body to dispense medication from the medication container. The medication container is movable relative to the housing between a storage position and a delivery position. The drive mechanism includes a plunger in engagement with the slidable piston. The drive mechanism is adapted to axially drive the plunger, to move the medication container from the storage position to the delivery position, and to move the slidable piston to dispense medication from the medication container in a dispensing event. The retraction mechanism is adapted to move the medication container from the delivery position to the storage position in a retraction movement. The retraction mechanism includes a rotary member configured to rotate during the retraction movement. The sensing system includes a first sensor disposed within the medication delivery device. The first sensor is configured to generate a plurality of first signals indicative of a first sensed parameter. The sensing system includes a second sensor disposed within the medication delivery device and positioned to sense rotational movement of the rotary member. The second sensor is configured to generate a plurality of second signals indicative of sensed rotational movement of the rotary member. A controller is operably coupled with the first sensor and the second sensor. The controller is configured to determine initiation of the dispensing event based on the plurality of first signals generated by the first sensor, and configured to determine at least one of completion of the dispensing event and completion of the retraction movement based upon the plurality of second signals generated by the second sensor.

In accordance with an embodiment of the present disclosure, a method for determining an operational status of a medication delivery device is provided. The device includes a needle, a first sensor, a second sensor, a rotary sensor, and a retraction mechanism. The method includes one or more of the following steps. A step includes determining an initiation of the dispensing event from a needle in an extended position based on a signal spike of a plurality of first signals generated by a first sensor. A step includes determining an end of the dispensing event from said needle in the extended position based on an initial spike of a plurality of second signals generated by a second sensor sensing rotation of a rotary member of a retraction mechanism. A step includes determining an end of a needle retraction of said needle from the extended position based upon a predetermined spike of second signals, subsequent to the initial spike of the second signals, generated by the second sensor. A step includes indicating on a user interface at least one of the determined initiation of the dispensing event, the determined completion of the dispensing event, and the determined completion of the needle retraction.

In accordance with an embodiment of the present disclosure, a medication delivery device includes a housing, a medication container, a drive mechanism, a retraction mechanism, an accelerometer, and a controller. The medication container includes a container body to hold a medication and a slidable piston operably coupled with the container body, the slidable piston movable relative to the container body to dispense medication from the medication container. The medication container is movable relative to said housing between a storage position and a delivery position. The drive mechanism is adapted to, when a dispensing event is initiated, drive the medication container from the storage position until the medication container stops at the delivery position. The retraction mechanism is adapted to, when a retraction movement is initiated, drive the medication container from the delivery position until the medication container stops at the storage position. The accelerometer is disposed within the medication delivery device, and is configured to detect a first acceleration caused by the medication container as it is driven from the storage position to the delivery position by the drive mechanism, and configured to detect a second acceleration caused by the medication container as it is driven from the delivery position to the storage position by the retraction mechanism. The controller is operably coupled with the accelerometer, and is configured to determine initiation of the dispensing event based on the detected first acceleration, and completion of the retraction movement based on the detected second acceleration.

BRIEF DESCRIPTION OF THE DRAWINGS

The above mentioned and other features of this disclosure, and the manner of attaining them, will become more apparent and the disclosure itself will be better understood by reference to the following description of embodiments of the disclosure taken in conjunction with the accompanying drawings, wherein.

Figure 1:
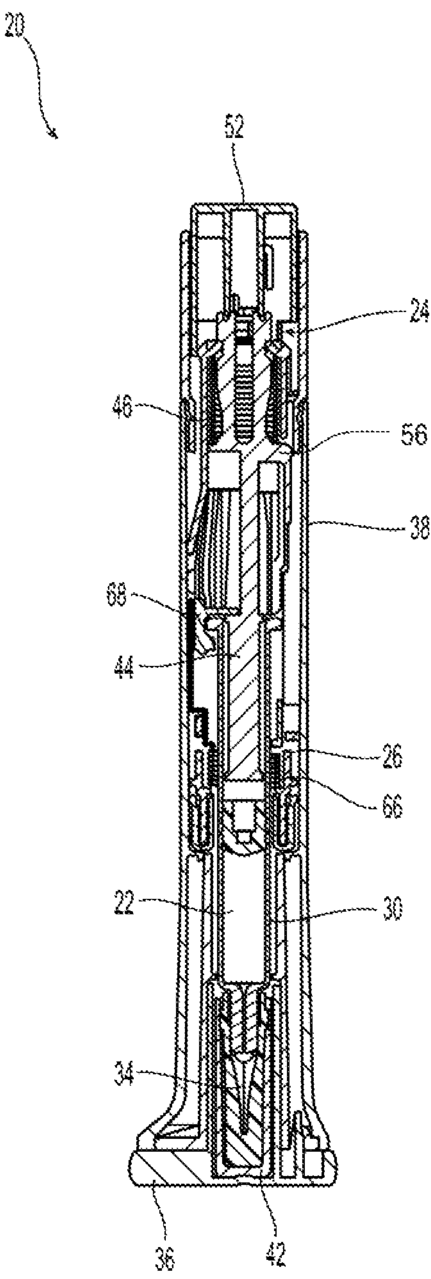
FIG. 1 is a cross sectional side view of an exemplary medication delivery device including an exemplary sensing system prior to use.

Corresponding reference characters indicate corresponding parts throughout the several views. Although the exemplification set out herein illustrates an embodiment of the disclosure, in one form, the embodiment disclosed below is not intended to be exhaustive or to be construed as limiting the scope of the disclosure to the precise form disclosed.

DETAILED DESCRIPTION

The automatic injection apparatus, generally designated 20, has a trigger that when actuated by a user results in the needled syringe of the apparatus automatically being driven downward such that the injection needle projects beyond the bottom end of the apparatus housing to penetrate the user. The apparatus then proceeds to inject automatically the medication contents of the syringe through the needle, after which the syringe is retracted automatically such that the injection needle is returned to within the housing. The delay mechanism of the apparatus helps to stage the operation to ensure that the medication contents are properly delivered prior to the needled syringe being retracted. When a device includes a hidden needle, the user may be provided operational status of the device via an indicator display or lights and/or sounds for each step of the process during the entire cycle of the drug delivery. Furthermore, the recordation and/or communication of drug delivery events or malfunctions may be provided with the device to patients and medical professionals. As used herein, the terms "distal" and "proximal" refer to axial locations relative to a user and opposite to an injection site when the apparatus is oriented for use at such site. For example, proximal end of the housing refers to the housing top end that is farthest to such injection site, and distal end of the housing refers to the housing base or injection end that is closest to such injection site.

Figure 2:
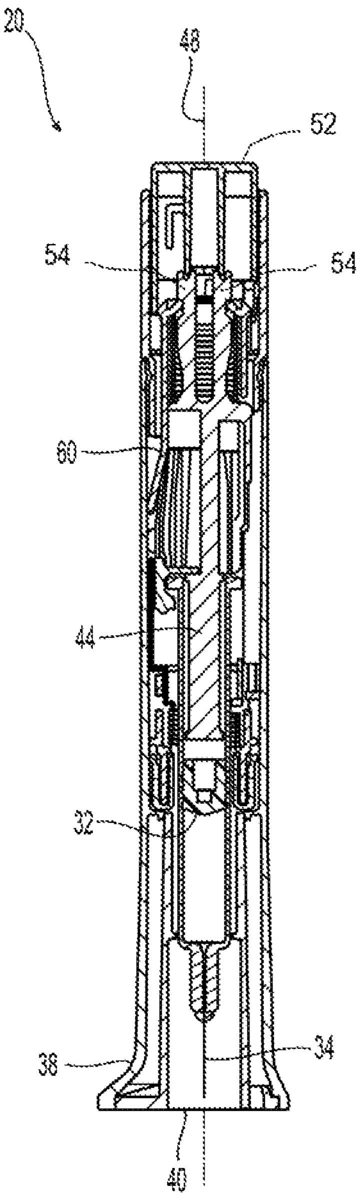
FIG. 2 is a cross sectional side view of the medication delivery device of FIG. 1 with the medication container in a storage position and ready for a dispensing event.
Figure 3:
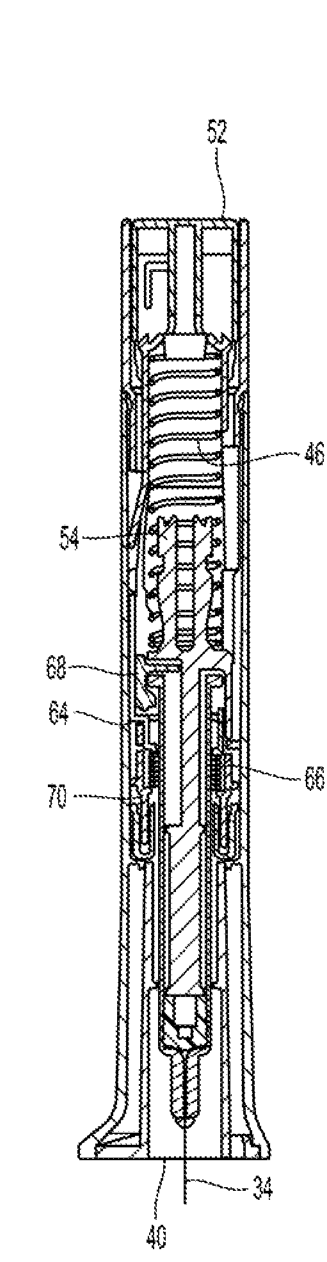
FIG. 3 is a cross sectional side view of the medication delivery device of FIG. 1 with the medication container in a delivery position.
Figure 11:
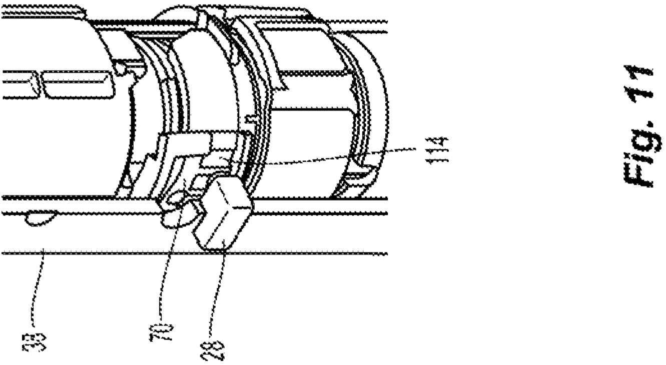
FIG. 11 is another partial cut-away perspective view of the medication device of FIG. 1 showing the sensing system with the rotary member of the retraction mechanism in a different position.
Figure 10:
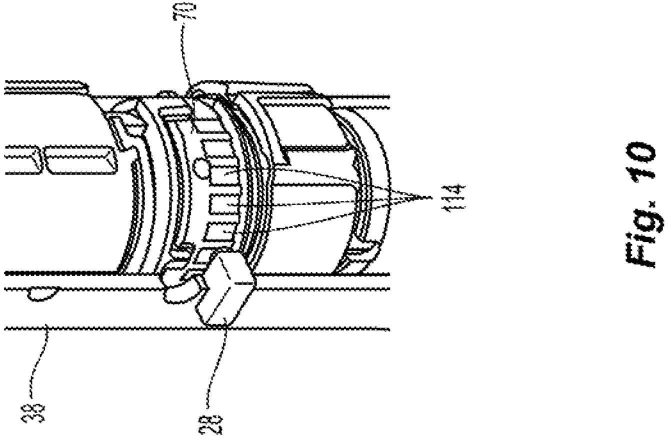
FIG. 10 is a partial cut-away perspective view of the medication delivery device of FIG. 1 showing an exemplary sensing system and a rotary member of a retraction mechanism in a first position.

An exemplary medication delivery device 20 is depicted in FIGS. 1-3. Device 20 includes a syringe system 22, a drive mechanism, generally designated 24, a retraction mechanism 26 and a sensing system 28 (depicted in FIGS. 10-11) coupled within a device tubular housing 38. The device 20 includes a delay mechanism including a shuttle assembly 60 to help stage the operation to ensure that the medication contents are properly delivered prior to the needled syringe being retracted. Syringe system 22 includes a container barrel body 30, such as made of glass or other suitable material, configured for holding a medication, a slidable piston member 32, such as an elastomeric sealing member, operably coupled with container body 30, and a hollow injection needle 34. The proximal end of injection needle 34 is mounted to a distal tip end of the barrel body 30. Injection needle 34 is in fluid communication with the medication contents of the syringe barrel body 30 and initially coverable by a needle guard 42. Distally advancing piston member 32 within barrel body 30 toward injection needle 34 dispenses medication through needle 34. Drive mechanism 24 is operably coupled to the piston member 32. Slidable movement of piston member 32 relative to container body 30 as a result of operation of the drive mechanism 24, as will be described, dispenses medication from the syringe system 22. The operation of drive mechanism 24 and retraction mechanism 26 in device 20 and other description of the components of an exemplary device are described in U.S. Pat. No. 8,734,394 to Adams et al., filed Feb. 24, 2011, the disclosure of which is hereby incorporated herein by reference.

FIG. 1 illustrates medication delivery device 20 in a storage configuration. A syringe overcap 36 is secured to housing 38 and covers a distal opening 40 in housing 38. Needle guard 42 is mounted on the distal tip end of barrel body 30 of syringe 22 to cover needle 34. Overcap 36 and needle guard 42 protect the user from accidental needle pricks and also protect needle 34 from damage. When using device 20 to dispense medication, for example, injecting the medication into a patient, overcap 36 and needle guard 42 are first removed to expose the distal opening 40. FIG. 2 illustrates device 20 after removal of overcap 36 and needle guard 42 with syringe 22 in a storage position and device 20 ready for a dispensing event.

Syringe system 22 is movable relative to the medication delivery device 20 between the storage position, shown in FIGS. 1-2, and a delivery position, shown in FIG. 3. FIG. 3 illustrates device 20 after the syringe system 22 has been moved relative to device 20 to a delivery position from its storage position. In the storage position, injection needle 34 is at a retracted position within device 20 in a manner where the distal tip of needle 34 does not extend beyond the distal opening 40. In the delivery position, the distal tip of needle 34 projects distally beyond the distal opening 40 from device 20 at an extended position for operable insertion into a patient.

Drive mechanism 24 includes a plunger 44 for an engagement relationship with piston member 32. Drive mechanism 24 includes a drive spring 46 that when released drives plunger 44 in a translational distal movement. In an example, spring 46 advances plunger 44 along a linear path defined by the central axis 48 of device 20. Plunger 44 includes a distal region with a disc-shaped foot 50 (FIG. 4) at one end that serves to operationally abut sealing piston 32 during plunger advancement. As the plunger 44 is further advanced, syringe 22 is advanced along axis 48 from its storage position to its delivery position. Drive spring 46 directly biases the plunger 44 downward to drive it and thereby piston 32 distally, which driven motion shifts syringe 22 distally relative to the shuttle assembly 60 and the housing 38 to cause the tip of needle 34 to project beyond housing distal end for penetrating a user's skin, and then forces the medication contents of the syringe through that needle for an injection. After advancement of syringe 22 to its delivery position, the continued advancement of plunger 44 advances piston 32 within barrel 30 to cause medication to be dispensed from needle 34 in a dispensing event. The advancement of plunger 44 will generally not result in the dispensing of medication from syringe 22 until after syringe 22 has been advanced to the delivery position. Two main factors inhibit the medication from being dispensed before the syringe is advanced to the delivery position for dispensing. First, is the friction between piston 32 and barrel 30. Typically, piston 32 will be formed out of a rubber material and barrel 30 will be glass. The frictional resistance between these two components may be sufficient to prevent the advancement of piston 32 within barrel 30 until syringe 22 is advanced to its delivery position and engagement with a suitable stop member prevents the further advancement of syringe 22. Additionally, the medication within the syringe may be somewhat viscous and thereby somewhat resistant to flowing out of needle 34. If necessary, modification of the piston member 32 and container body 30 to alter the frictional resistance of the piston member 32 relative to container body 30 can limit or prevent the premature dispensing of medication before syringe 22 reaches its delivery position.

At the top or proximal end of the housing 38 and protruding axially therefrom, a safety-controlled button 52 that is part of the user-operated trigger is provided. When a safety sleeve of the housing is disposed in a proper angular orientation relative to the housing 38 as rotatably adjusted by the user, button 52 is unlocked and can be depressed to start the automatic injection function of the apparatus. To activate drive mechanism 24, a person will depress actuating button 52 at the proximal end of device 20. Depressing button 52 disengages one or more elongate prongs 54 of plunger 44 from a shuttle assembly 60 thereby allowing spring 46 to axially advance plunger 44. Spring 46 has a helical shape and surrounds prongs 54. The distal end of spring 46 biasingly engages a flange 56 on plunger 44.

Figure 4:
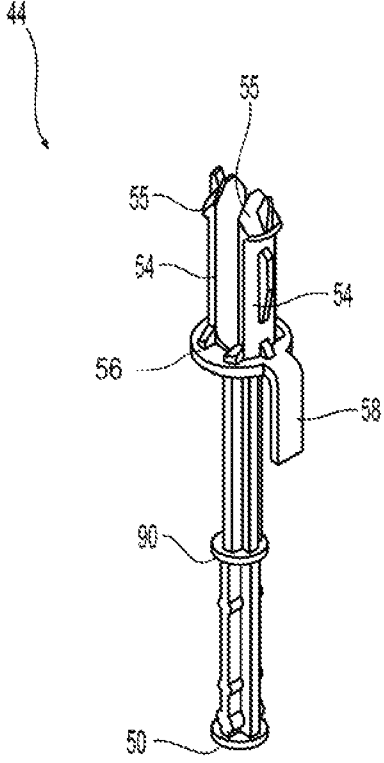
FIG. 4 is a perspective view of an example of a plunger provided with the medication delivery device of FIG. 1.
Figure 6:
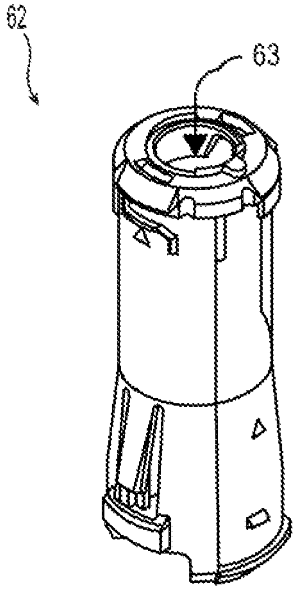
FIG. 6 is a perspective view of an example of an upper shuttle member provided with the medication delivery device of FIG. 1.

FIG. 4 illustrates an example of plunger 44. The proximal region of the plunger includes one or more prongs (a pair of prongs 54 shown). The prongs 54 are configured to flex radially inward. In another example, the plunger includes a single prong. The foot 50 is located along a distal end of the plunger. Ramped surfaces 55 may be formed along the tips of the prongs. An outrigger 58 distally depends from flange 56 of plunger 44 in a spaced relationship from the plunger body. Outrigger 58 during an injection directly engages a locking member to unlock a rotary member 70 of the delay mechanism (depicted in FIG. 3). Rotary member 70 is also be a part of the retraction mechanism 26. The location of the outrigger 58 relative to plunger 44 and to the rotary member 70 is such that engagement between the outrigger and the rotary member corresponds to the completion of the dispensing event. Depressing button 52 causes tabs on button 52 to engage ramps 55 on prongs 54 to bias prongs 54 inwardly to disengage prongs 54 from an upper shuttle member 62 (depicted in FIG. 6) of shuttle assembly 60 (depicted in FIG. 2) to correspond to an initiation of the dispensing event. After prongs 54 have been disengaged, spring 46 exerts a biasing force on flange 56 to advance plunger 44 from the first position shown in FIG. 2 where the piston is at a proximal end of the container barrel body 30 to the final fully extended position shown in FIG. 3 where the piston is at a distal end of the container barrel body 30.

Figure 7:
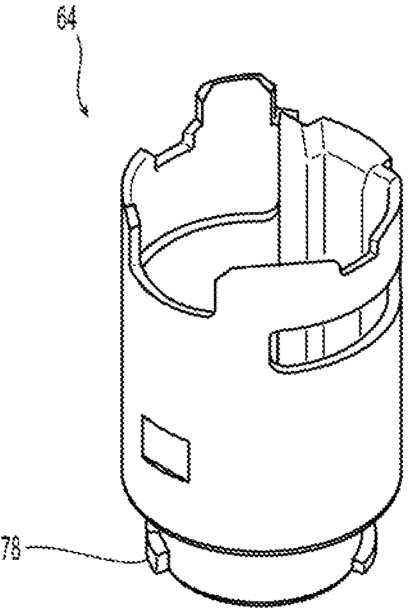
FIG. 7 is a perspective view of an example of a lower shuttle member provided with the medication delivery device of FIG. 1.
Figure 9:
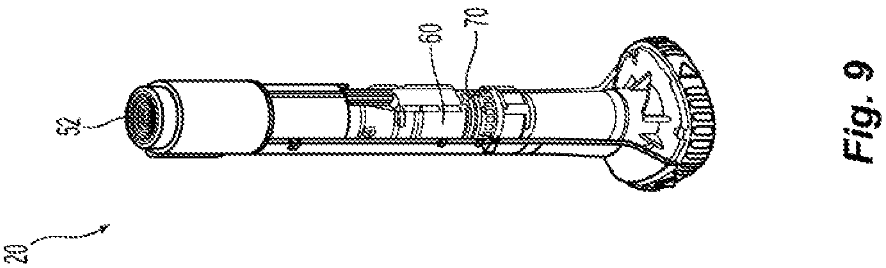
FIG. 9 is a partially cut-away perspective view of the medication delivery device of FIG. 1.
Figure 8:
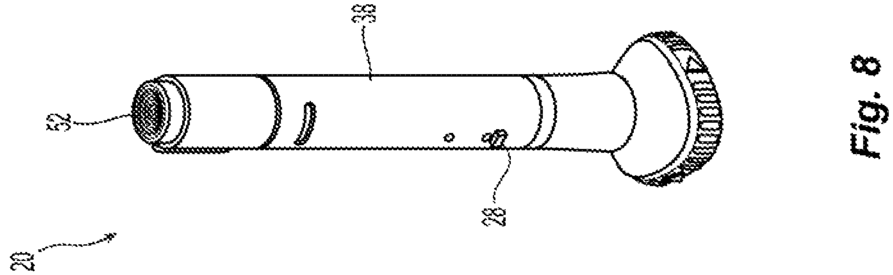
FIG. 8 is a perspective view of the medication delivery device of FIG. 1.

The delay mechanism of device 20 includes the shuttle assembly 60 (labeled in FIG. 2), rotary member 70 (labeled in FIG. 3) that releasably latches with the shuttle assembly 60, and a spring 66 (labeled in FIG. 1) acting between the shuttle and the rotary member. The shuttle assembly 60 may be formed of a single piece shuttle. In the shown embodiment, shuttle assembly 60 is formed of an upper shuttle 62 and a lower shuttle 64 further shown in FIG. 6 and FIG. 7, respectively. Shuttle parts 62 and 64 may be fixedly connected during manufacturing assembly, such as with a snap fit or other suitable connection manner, to together serve as the shuttle assembly. The multi-piece construction facilitates molding and assembly of the shuttle, as well as the assembly of the apparatus components within the interior hollow of the shuttle. Suitable materials for any one of the shuttle parts is a plastic such as, for example, polycarbonate or alloy thereof that is transparent.

In the final assembly, upper shuttle member 62 captures button 52 and spring 46 limiting the axial movement of these parts in the proximal direction. The upper and lower shuttle members 62, 64 each includes a tubular, cylindrical body. A central aperture 63 extends through the upper and lower shuttle member bodies to allow passage of the latching portion of plunger prongs 54. Guide features, such as dogs, project proximally from the upper surface of upper shuttle member 62 around aperture 63 and help guide activating tabs of button 52 into aperture 63 during use. Prongs 54 engage upper surfaces of upper shuttle 62 when the device is in the condition shown in FIGS. 1 and 2. Depressing button 52 distally moves tabs of button 52 to engage ramps 55 on prongs 54 to bias prongs 54 inwardly to disengage prongs 54 from upper shuttle member 62. After prongs 54 have been disengaged and positioned within the cross-sectional area of the aperture 63, spring 46 exerts a biasing force on flange 56 to advance plunger 44 from the first position shown in FIG. 2 to the second position shown in FIG. 3. As plunger 44 is advanced, syringe 22 is advanced to the delivery position and then the piston 32 is distally advanced within syringe 22 to dispense medication as discussed above.

After the dispensing event is complete, retraction mechanism 26 is configured to proximally move syringe 22 from the delivery position shown in FIG. 3 back to the storage position shown in FIG. 2 or a more proximal position such that the housing covers the needle. In the illustrated embodiment, the retraction mechanism having the delay mechanism includes the spring 66, a syringe carrier 68 shown in FIG. 5 and the rotary member 70 that acts as a follower.

Outrigger 58 of plunger 44 unlocks rotary member 70 as plunger 44 nears the end of its travel in the distal direction. With additional reference to FIGS. 12-13, rotary member 70 is rotationally secured to lower shuttle member 64 by engagement between latch 72 and a latching recess in lower shuttle member 64. Outrigger 58 unlocks member 70 by depressing latch 72. Spring 66 is torsionally preloaded and has a distal end engaged with rotary member 70 and an opposite proximal end engaged with shuttle assembly 60. Upon depression of latch 72, spring 66 causes rotary member 70 to rotate. Member 70 includes a slot 74 (shown in FIG. 12) that receives a tab 78 of lower shuttle member 64 (shown in FIG. 7). At one end of circumferential slot 74 formed in the body of the rotary member 70, an axially extending channel 76 is defined in the rotary member body. Relative rotation between rotating member 70 and lower shuttle member 64, moves tab 78 moves within slot 74 until tab 78 reaches axially extending channel 76. At this position, the biasing spring 66 urges axial separation between the rotary member 70 and the lower shuttle member.

Member 70 is rotatable within housing 38 about the axis 48 but is axially fixed relative to housing 38 and the shuttle assembly 60. An outer radial flange 82 defined along a body section of rotary member 70 is configured to engage an inner ledge defined along the interior surface of housing member 38 to limit the axial movement of member 70. Spring 66 exerts an axial force and/or torsional force on member 70 to bias member 70 distally to thereby maintain member 70 in an axial position where flange 82 engages the interior ledge of housing member 38. Shuttle assembly 60 includes axially extending channels and/or ribs that engage corresponding guiding features defined along the interior of housing member 38 that allow shuttle assembly 60 to move axially within housing 38 and inhibit the relative rotation between shuttle assembly 60 and housing member 38.

Spring 66 is also axially preloaded and exerts a proximally directed biasing force on shuttle assembly 60. Rotation of rotary member 70 about lower shuttle member 64 is driven by spring 66 until channel 76 align with shuttle tabs 78, respectively. In this arrangement, tabs 78 are clear of ledges that form slot 74 such that shuttle assembly 60 and rotary member 70 are unlatched. When tab 78 reaches channel 76, spring 66 moves shuttle assembly 60 proximally within housing 38 as tab 78 slides axially through channel 76. A damping compound may be arranged adjacent rotary member 70 to control, such as slowing, the rotation of member 70 and allow for the completion of the dispensing event before tab 78 reaches channel 76. In the illustrated embodiment, rotary member 70 includes a skirt with a plurality of axially extending tabs 80 extending below the ledge 82, which are disposed in a grease collar to provide damping.

As shuttle assembly 60 moves proximally, it carries syringe 22 proximally and moves it back to the storage position shown in FIG. 2. Spring 66 biases the retraction mechanism 26 proximally and thereby maintains syringe 22 in its storage position after a dispensing event. A locking mechanism such as a detent on the shuttle assembly 60 and a recess on the housing member 38 may additionally provide a locking engagement to secure syringe 22 in the storage position after a dispensing event whereby the user can then dispose or otherwise handle device 20 in a safe manner.

Figure 5:
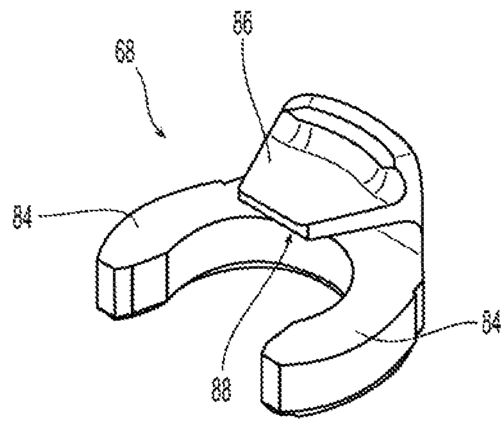
FIG. 5 is a perspective view of an example of a syringe carrier provided with the medication delivery device of FIG. 1.

Syringe carrier 68 is shown in FIG. 5. Arcuate arms 84 grip barrel 30 of syringe 22. Syringe carrier 68 also includes a radial flange 86 spaced above the arms 84 from a circumferential base. A flange on the syringe barrel 30 is captured between arms 84 and flange 86. A portion of the underside 88 of flange 86 engages small flange 90 on plunger 44 and thereby prevents proximal axial movement of syringe 22 before plunger 44 is advanced. When shuttle assembly 60 is being retracted, lower shuttle member 64 engages arms 84 to carry syringe 22 proximally back to its storage position.

Sensing system 28 is operable to detect and/or display or indicate operational status steps to a user or other person. In one example, the sensing system 28 includes a sensor for detecting an initial status of the injection process. In another example, the sensing system 28 includes a sensor for detecting intermediate and final status of the injection process. In another example, the sensing system 28 includes a sensor for detecting all the above-mentioned statuses of the injection process. In another example, the sensing system 28 includes a first sensor for detecting an initial status of the injection process, and a second sensor for detecting intermediate and final status of the injection process. In one example in FIG. 14, the first sensor includes an accelerometer 92 and the second sensor includes an optical sensor 94. The optical sensor 94 includes a light emitter 96 and a light sensor 98. In one example, the accelerometer 92 is associated with the device housing 38 at a location to sense acceleration and/or movement of a relevant component and not interfere with movable components. For example, the accelerometer may be embedded on the device housing 38 or otherwise affixed along the interior of the device housing 38. In one example, the optical sensor 94 is associated with the device housing 38 at a location to sense an encoded pattern of a relevant component and not interfere with movable components. For example, the optical sensor 94 may be embedded on the device housing 38 or otherwise affixed along the interior of the device housing 38. In another example, the accelerometer 92 and the optical sensor 94 may be associated with a single control module, such as shown in FIG. 14.

Various sensor systems are contemplated herein. In general, the sensor systems comprise one or more sensing components and one or more sensed components. The term "sensing component" refers to any component which is able to detect the relative position of the sensed component. A sensing component includes one or more sensing elements, or "sensors", along with associated electrical components to operate the one or more sensing elements. A "sensed component" is any component for which a sensing component is able to detect the position and/or movement of the sensed component relative to the sensing component. For example, the sensed component may axially move and/or rotate relative to the sensing component, which is able to detect the linear and/or angular position and/or the linear and/or rotational movement of the sensed component. The sensing component may include one or more sensing elements, and the sensed component may include one or more sensed elements. The one or more sensing components of a sensor system is/are able to detect the position or movement of the sensed component(s) and to provide outputs representative of the position(s) or movement(s) of the sensed component (s). A sensor system typically detects a characteristic of a sensed parameter which varies in relationship to the position and/or movement of the one or more sensed elements within a sensed area. The sensed elements extend into or otherwise influence the sensed area in a manner that directly or indirectly affects the characteristic of the sensed parameter. The relative positions of the sensing component(s) and the sensed component(s) affect the characteristics of the sensed parameter, allowing the controller of the sensor system to determine different positions of the sensed element(s). Suitable sensor systems may include the combination of an active component (e.g., powered or connected to a power supply or controller) and a passive component (e.g., that is not powered or connected to a power supply or controller). Either the sensing component or the sensed component may operate as the active component. If one component is operating as an active component, the other component need not operate as an active component and may instead operate as a passive component. Any of a variety of sensing technologies may be incorporated by which the relative positions of two members can be detected. Such technologies may include, for example, technologies based on tactile, optical, inductive or electrical measurements. Such technologies may include the measurement of a sensed parameter associated with a field or electrical parameter, such as an electric/magnetic field. In one form, a magnetic sensor senses the change in a sensed magnetic field as a magnetic component is moved relative to the sensor. In another embodiment, a sensor system may sense characteristics of and/or changes to an electric/magnetic field as an object is positioned within and/or moved through the magnetic field. The alterations of the field change the characteristic of the sensed parameter in relation to the position of the sensed element in the sensed area. In such embodiments the sensed parameter may be a capacitance, conductance, resistance, impedance, voltage, inductance, etc. For example, a magneto-resistive type sensor detects the distortion of an applied magnetic field which results in a characteristic change in the resistance of an element of the sensor. As another example, Hall effect sensors detect changes in voltage resulting from distortions of an applied magnetic field. In one example, the second sensor is a magnetic sensor and the rotary component includes a magnetic property.

Figures 12, 13, 14:
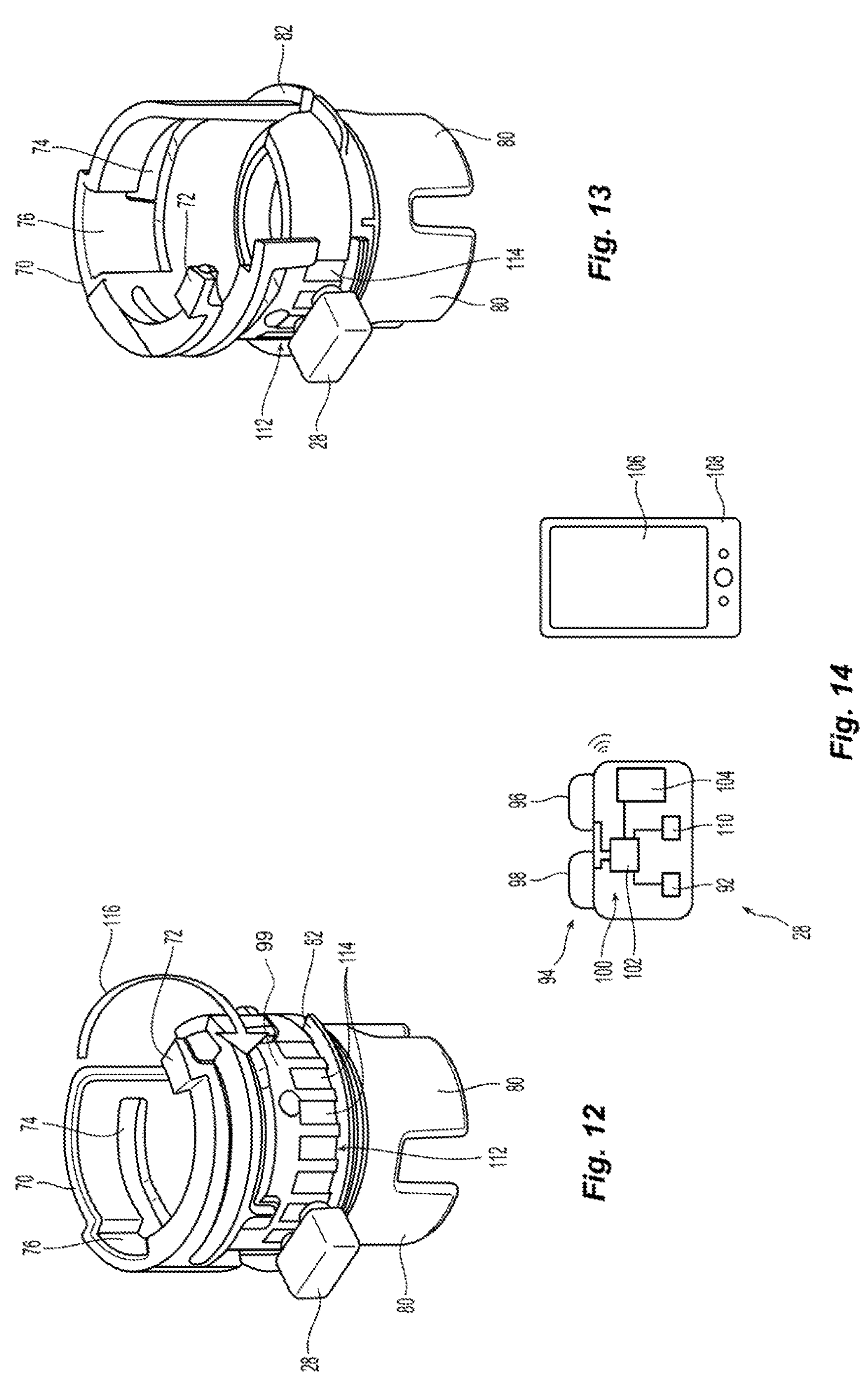
FIGS. 12-13 are perspective views of the sensing system and the rotary member, depicting operation of the respective components, with the surrounding components of the medication delivery device of FIG. 1 removed.
FIG. 14 is a schematic view of the sensing system communicating data to an exemplary external separate device.

In FIGS. 12-13, an encoder strip 112 is formed along the outer circumferential surface 99 of the rotary member 70. In one example, the encoder strip is axially disposed along the exterior body of the rotary member 70 between the ledge 82 and the slot 74. The encoder strip 112 includes a plurality of targets 114 disposed circumferentially spaced from one another and recognizable by the optical sensor 94 of sensing system 28. For example, targets 114 may be formed by discretely recognizable targets using a different color for the targets and the space between the targets. In another example, the targets comprise a continuous gradient of two distinct colors to provide a variable signal. Alternatively, the targets 114 may be given a different surface treatment. For example, targets 114 could be given a rough surface treatment to scatter light while the spaces between targets 114 are smooth and reflective.

Sensor system 28 also includes a controller 100 having an electronic circuit having a processor 102, clock or timer (not shown) for date/time tracking and stamping, and a storage device (not shown). Data may be stored in the storage device, such as, for example, RAM, PROM, optical storage devices, flash memory devices, hardware storage devices, magnetic storage devices, or any suitable computer-readable storage medium. The data may be accessed and operated upon according to instructions from the processor 102.

The accelerometer 92 and optical sensor 94 are both electronically connected with controller 100 and operably coupled with processor 102. Sensor system 28 may optionally include a user interface 104. User interface 104 may take the form of an LCD screen or, in a more simplified form, one or more LED lights. System 28 also includes a power source 110 that powers sensors 92, 94, processor 102 and user interface 104 if it is present. User interface may be a separate display screen located along the device housing. If device 20 is a disposable device designed for a single injection procedure, power source 110 may be sized to provide sufficient power only for a single procedure. A rechargeable or easily replaceable power source, such as a rechargeable or disposable battery, may be employed if device 20 is intended for multiple uses. In the illustrated embodiment, device 20 is a single use, disposable device.

Controller 100 may include a communication unit (such as transmitter and/or receiver or transceiver) for communicating with a separate device 106 as schematically depicted in FIG. 14. The separate device 106 may take the form of a smart phone having a user interface 108. The communication unit (not shown) is configured to communicate one-way or two-way with the separate device 106 which includes a user interface 108 that can communicate the occurrence of these events. In one example, the communication unit includes a low power radio-frequency wireless transceiver utilizing a wireless technology standard for exchanging data, such as for example, based on IEEE 802.15 standards, including, but not limited to, Bluetooth (e.g., Bluetooth Standard, low-energy, and Smart) and Zigbee, the ANT and ANT+ protocols, or near field communication (NFC) using a NFC chip. Other suitable wireless communication protocols such as WI-FI may be used. Although it will generally be most convenient to wirelessly communicate with a separate device, it would also be possible to use a wired connection for such communications. The device housing may include an electrical connector (not shown) operably connected with the controller. The electrical connector may be configured as a USB connector (such as, for example, Series Standard-A, Standard-B, Standard-C, Mini-A, Mini-B, Micro-A, or Micro-B connector), serial port connector, a video graphics array (VGA) connector, a D-subminiature connector, a BNC connector, or a mini-DIN connector. Furthermore, the electrical connector may by a male or female connector.

As can be most easily seen in FIGS. 8-11, sensor system 28 is mounted on housing such that accelerometer 92 is disposed on the medication delivery device and can sense motion and velocity of housing 38 or a component within housing 38. When spring 46 acts on plunger 44 after the user depresses actuating button 52 to initiate the dispensing event, drive spring 46 accelerates plunger 44 and syringe in the distal direction until the syringe 22 hits an axial stop at its delivery position, abruptly halting any more distal movement. This change in acceleration action generates movement and forces that are sensed by accelerometer 92. The timing of the syringe 22 arriving at its delivery position and the movement of piston 32 for dispensing the medication through the needle may be predetermined and precise. In other words, the initiation of the dispensing event may be associated with the arrival and abrupt stop of the syringe at its delivery position. The retraction event occurs to move the syringe from its delivery position to its storage position. The upward (proximal) acceleration of the syringe during a retraction event imparts a small acceleration in the opposite direction to the injector body. By detecting and analyzing the timing and magnitude of these features, the initiation of the dispensing event and the initiation and/or completion of the retraction event may be detected, and variations in the syringe advance and retract performance could be detected.

Figure 15:
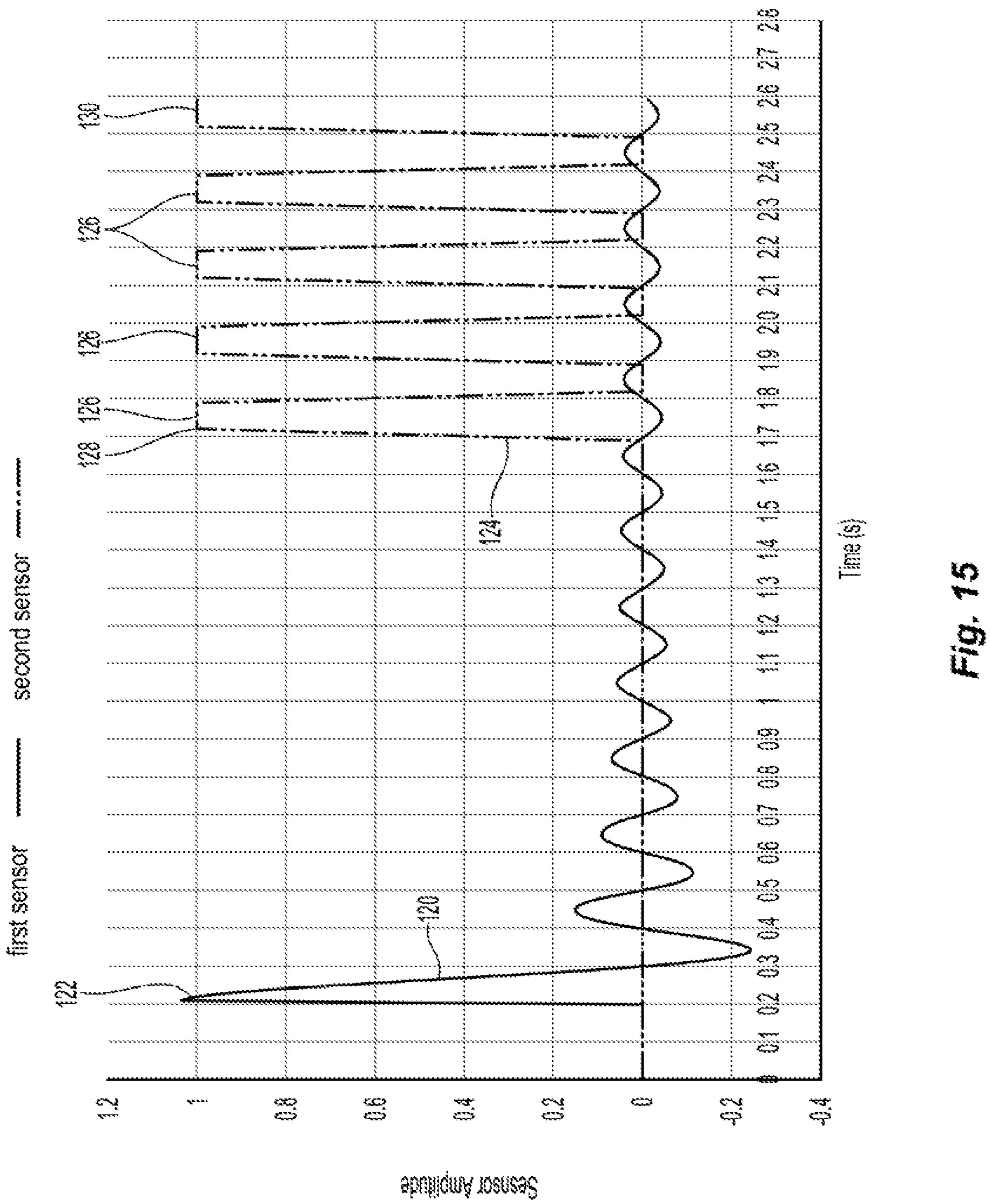
FIG. 15 is a chart illustrating signals generated by sensors of the sensing system.

The chart presented in FIG. 15 provides a simplified representation of the output of sensors 92, 94. Line 120 represents the signals generated by accelerometer 92, which are indicative of the sensed acceleration and are communicated to processor 102. Spike 122 in the accelerometer signals represents the initiation of a dispensing event when the movement of syringe 22 into the delivery position is abruptly halted. The further advancing plunger 44 moves piston 32 for dispensing medication from syringe 22. As the dispensing event begins, the vibration of housing 38 caused by the stopping of syringe 22 decreases in magnitude as shown by line 120.

As plunger 44 nears the end of its distal advancement, outrigger 58 on plunger 44 unlocks rotary member 70 which then begins to rotate about axis 48 as discussed in greater detail above. Optical sensor 94 may be positioned to sense rotational movement of rotary member 70 by sensing the passage of individual targets 114. Optical sensor 94 generates signals indicative of this sensed rotational movement of rotary member 70 and communicates these signals to processor 102. Dashed line 124 in the chart of FIG. 15 represents the signals generated by optical sensor 94. Also, when plunger 44 unlocks rotary member 70 and allows member 70 to begin rotating, this initiates the retraction movement of retraction mechanism 26. This retraction movement results in the movement of syringe 22 from its delivery position (FIG. 3) to its storage position (FIG. 2).

As best seen in FIGS. 12 and 13, optical sensor 94 is positioned to monitor the rotational movement of member 70. FIG. 12 represents the position of optical sensor 94 relative to member 70 at the time when rotational movement of member 70 is initially started. Arrow 116 shows the direction in which member 70 will rotate relative to sensor assembly 28. As member 70 rotates, targets 114 of encoder strip 112 are recognized by optical sensor 94 as the individual targets 114 rotate past optical sensor 94. FIG. 13 shows member 70 when it has completed its rotational movement and tab 78 is aligned with channel 76 such that shuttle 60 is retracted distally by spring 66 and returns syringe 22 to its storage position.

Line 124 in FIG. 15 represents the signals communicated by optical sensor 94. In one example, the optical sensor signals are binary signals such that the absence of signal (value 0 in FIG. 15) indicates that the sensor does not sense a target 114 and the communication of a signal (value 1 in FIG. 15) indicates that the sensor recognizes a target. Thus, line spike portions 126 of the sensor signal in FIG. 15 represent the passage of a target 114 past optical sensor 94. In another example, the encoder strip 112 may include a continuous gradient from black to white such that the optical sensor signals are variable signals. In an example, the optical sensor 94 may configured to communicate an analog value sampled by the controller 100 to provide finer grain resolution for rotational position and velocity.

When optical sensor 94 first recognizes the passage of a target 114 as represented by initiation spike point 128 of line 124, this represents when rotary member 70 has been unlocked and has just begun to rotate. Thus, this point also corresponds to the completion of the dispensing event. In this regard, it is noted that the completion of the dispensing event may correspond directly with the point in time represented by point 128, or, have a known correlation to this point in time, e.g., the completion of the dispensing event may occur 0.2 seconds after the point in time represented by point 128. In either event, point 128 signifies that the retraction movement of retraction mechanism 26, such as rotation of rotary member 70, has begun.

The arc through which member 70 must rotate to complete its rotational movement and align channel 76 with tab 78 is known in advance. Thus, the number of targets 114 which must pass by optical sensor 94 for member 70 to complete its rotational movement can also be known in advance. In the illustrated embodiment, when the fifth target 114 is recognized by sensor 94, as indicated by reference numeral 130 in FIG. 15, rotary member 70 will have completed its rotational movement and aligned channel 76 with tab 78. Once this occurs, shuttle member 60 will be moved proximally and syringe 22 will be moved to its storage position to complete the retraction movement. In this regard, it is noted that the completion of the retraction event may correspond directly with the point in time represented by point 130, which may also correspond to a complete end of the operational cycle of the device. Alternatively, the completion of the retraction event may have a known correlation with the point in time represented by point 130, e.g., the completion of the retraction event may occur 0.2 seconds after the point in time represented by point 130.

In the illustrated embodiment, and as discussed above, controller 100 is configured to detect initiation of the dispensing event based on the signals generated by accelerometer 92. More specifically, controller 100 is configured to determine the initiation of the dispensing event based on spike 122 of the signal generated from the accelerometer 92. Controller 100 is also configured to determine completion of the dispensing event and completion of the retraction movement based upon the signals generated by optical sensor 94. For example, controller 100 is configured to determine the initial recognition of rotary movement based on the initial point 128 of the signal line 124 as the completion of the dispensing event (either with or without correction). Controller 100 is configured to determine the final recognition of rotary movement based on the point 130 of the signal line 124 as the completion of the retraction event (either with or without correction). In one example, controller 100 may also count the number of targets recognized by sensor 94 and when the appropriate number of targets has been counted to indicate that member 70 has fully completed its rotational motion, controller 100 interprets this as the completion of the retraction movement and the successful return of syringe 22 to its storage position. Controller 100 may be configured to detect end of the dispensing or retraction event based on the signals generated by accelerometer 92, which can be independent to or in addition to the optical sensing signal at point 130. When the needle is retracted under a spring force based on the position of the rotary member 70, the sudden stop of the subassembly within the device when reaching the final retracted position produces a detectable acceleration. More specifically, controller 100 is configured to determine the ending event based on a spike or valley (not shown in FIG. 15 but approximately located at time 26 sec) of the signal generated from the accelerometer 92. When using both the accelerometer and the optical sensing to detect end of delivery cycle, the controller 100 may compare each of the signals for reliability or redundancy in detecting syringe position or travel malfunction. Other characteristics in the accelerometer 92 may be useful in detecting syringe position or travel malfunction. One occurs prior to the syringe 22 hitting the hard stop when moving to the extended position. As the drive spring 46 initially accelerates the syringe 22 forward, a small acceleration is imparted to the injector housing 38 and may be detected. Another characteristic occurs when the rotary member 70 allows the dual functioning biasing member 66 to operate. The upward acceleration of the syringe 22 imparts a small acceleration in the opposite direction to the injector housing 38. By controller 100 detecting and analyzing the timing and magnitude of these features, the initiation of the dispensing event and the initiation and/or completion of the retraction event may be detected, and variations in the syringe advance and retract performance may be detected and indicated and/or communicated.

The operational status of the device determined from such information may be also communicated to the user. To this end, controller 100, in response to determining steps, is configured to generate an output signal for each of the determined steps for a display or other user feedback indication. For example, sensor system 28 may generate a signal indicative of the determined initiation of the dispensing event. Sensor system 28 may generate another signal indicative of the determined completion of the dispensing event. Sensor system 28 may generate another signal indicative of the determined initiation of the retraction movement. Sensor system 28 may also generate another signal indicative of the determined completion of the retraction movement. Any one or combination of these output signals may be communicated to the user interface 104 to thereby inform the user of occurrence of the initiation of the dispensing event, the completion of the dispensing event, the initiation of the retraction movement, and/or the completion of the retraction movement. For example, an LCD screen or LED lights on device 20 could communicate the occurrence of these events.

In addition to simply recognizing when certain events occur, controller 100 may also be configured to analyze the sensor signals to identify malfunctions. In one example, controller 100 is configured to monitor the signals from optical sensor 94 to ensure that rotary member 70 has fully completed its rotation to allow syringe 22 to be retracted to the storage position. If rotary member 70 does not rotate through a sufficiently large rotational arc (for example, only three of five lines 126 of signal line 124 in FIG. 15 are monitored), controller 100 may be configured to identify this as a malfunction in the retraction movement. If the signals generated by optical sensor 94 indicate that rotary member 70 did not fully complete its rotational movement, controller 100 may be configured to determine that the medication container was not successfully moved from the delivery position to the storage position in the course of a retraction movement.

Controller 100 may also be configured to determine the duration of a dispensing event based upon the time interval between spike 122 of the accelerometer signal 120 and the initiation point 128 of the optical sensor signal 124 (or the detection of an acceleration associated with a retraction event, as discussed above). If the duration of the dispensing event is shorter or longer than a predetermined threshold range, the processor may determine such event and flag it as a malfunction. Alternatively, if the duration falls within an acceptable range for the quantity of medication being dispensed, it may be considered to be a successful medication delivery. When a malfunction occurs, the controller 100 may be configured to communicate to the user interface for display of a warning or flashing of LEDs (red LEDs). Such event may recorded and communicated to a healthcare professional.

The information obtained from such signals may be recorded in memory along with the time and date of the medication dispensing event. This recorded data may then be communicated to a separate remote device 106 (such as, for example, mobile phone, laptop, and/or server database) or a caregiver via a wireless connection and/or the internet. Device 106 may keep a log of all such medication delivery events, including the date and time of the medication delivery event and whether or not any malfunctions were detected. Device 106 may also communicate such information through a network to a medical professional who may also maintain a log of such medication delivery events. Controller 100 may also be configured to record in memory and communicate the type of medication dispensed and the quantity. For single use, disposable devices, this information will be known in advance and the recordation thereby easily facilitates the communication of the type and quantity of the medication being delivered in a delivery event. The ability for a user to automatically generate a log of medication delivery events can be extremely useful for users who regularly inject medication and find it cumbersome or inconvenient to maintain a log of such medication delivery events.

As can be seen in the figures, except for encoder strip 112 located on rotary member 70, sensor system 28 is packaged in a single small housing mounted on housing 38. As such, it can be permanently mounted on a device 20 or detachable and re-used with multiple devices provided that such devices have a rotary member 70 with an encoder strip 112 and a mounting interface to accept sensor system 28.

In one example, an exemplary method for determining the operational status of the device 20 is provided. The method may include determining an initiation of the dispensing event. The controller 100 is configured to determine initiation of the dispensing event based on the first signals generated by the first sensor. When the first sensor is an accelerometer, the initial spike in the signal may be due to the abrupt stop of the syringe when it is moved from the storage position to the delivery position. Another step may include determining an end of the dispensing event. The arrangement of the outrigger of the plunger and the rotary follower is such that engagement between the outrigger and the rotary follower and thus the start of rotation of the follower is at the moment when the dispensing event is completed. The controller 100 is configured to determine completion of the dispensing event based upon an initial spike of second signals generated by the second sensor. Another step may include determining an end of the retraction and/or complete drug delivery cycle. The controller 100 is configured to determine completion of the retraction movement based upon the predetermined spike of second signals generated by the second sensor, or upon detection of an acceleration caused by retraction of the syringe into the device housing. The method may include indicating the determined initiation of the dispensing event, the determined completion of the dispensing event, the determined initiation of the retraction, the determined completion of the retraction or delivery cycle, or any combination thereof. The controller may be further configured to communicate any of the indicated events to an on-board user indicator or to a remote user indicator external to the device. The method may include determining a malfunction of the operation of the device. The controller may be configured to analyze parameters of the sensor based on the first and/or second signals from the respective sensors, compare such parameters to threshold ranges stored in the storage device, and if outside the threshold range, communicate any determined malfunction to an on-board user indicator or to a remote user indicator external to the device.

While this disclosure has been described as having an exemplary design, the present disclosure may be further modified within the spirit and scope of this disclosure. This application is therefore intended to cover any variations, uses, or adaptations of the disclosure using its general principles.

Various aspects are described in this disclosure, which include, but are not limited to, the following aspects:

1. A medication delivery device comprising: a housing; a medication container having a container body to hold a medication and a slidable piston operably coupled with the container body, the slidable piston movable relative to the container body to dispense medication from the medication container, the medication container being movable relative to said housing between a storage position and a delivery position; a drive mechanism including a plunger in engagement with the slidable piston, the drive mechanism being adapted to axially drive the plunger, to move the medication container from the storage position to the delivery position, and to move the slidable piston to dispense medication from the medication container in a dispensing event; a retraction mechanism adapted to move the medication container from the delivery position to the storage position in a retraction movement, wherein the retraction mechanism includes a rotary member configured to rotate during the retraction movement; and a sensing system including a first sensor disposed within the medication delivery device, the first sensor configured to generate a plurality of first signals indicative of a first sensed parameter, a second sensor disposed within the medication delivery device and positioned to sense rotational movement of the rotary member, the second sensor configured to generate a plurality of second signals indicative of sensed rotational movement of the rotary member, a controller operably coupled with the first sensor and the second sensor, wherein the controller is configured to determine initiation of the dispensing event based on the plurality of first signals generated by the first sensor, and configured to determine at least one of completion of the dispensing event and completion of the retraction movement based upon the plurality of second signals generated by the second sensor.

2. The device of aspect 1 comprising a user interface operably coupled to the controller, wherein the controller is configured to communicate the initiation of the dispensing event, and at least one of the completion of the dispensing event and the completion of the retraction movement to said user interface.

3. The device of aspect 2 wherein the user interface is disposed on the device.

4. The device of aspect 2 wherein the user interface is separate from the device, the controller configured to communicate the initiation of the dispensing event, and at least one of the completion of the dispensing event and the completion of the retraction movement wirelessly to the user interface.

5. The device of any one of aspects 1-4 wherein the controller is configured to determine a malfunction from analysis of at least one of the first signals and the second signals.

6. The device any one of aspects 1-5 wherein the controller is configured to determine a duration of a dispensing event based upon the first signals and the second signals.

7. The device any one of aspects 1-6 wherein the controller is configured to determine a malfunction from analysis of the second signals to determine if the medication container was unsuccessfully moved from the delivery position to the storage position when the device performs a retraction movement.

8. The device of aspect 7 wherein the second sensor is an optical sensor, and the rotary member defines a plurality of sensor targets recognizable by the optical sensor.

9. The device any one of aspects 1-8 wherein the sensor system is configured to record data for a dispensing event based upon the first signals and the second signals.

10. The device of aspect 9 wherein the sensor system is configured to communicate the recorded data to a separate device.

11. The device of aspect 10 wherein the recorded data communicated by the sensor system includes a date and a time of the dispensing event.

12. The device of 10 wherein the controller is configured to determine a malfunction from analysis of at least one of the first signals and the second signals.

13. The device any one of aspects 1-12 wherein the drive mechanism includes a spring for driving the plunger and the medication container, wherein the controller is configured to determine a malfunction from analysis of the second signals to determine if the medication container was unsuccessfully moved from the delivery position to the storage position when the device performs a retraction movement.

14. A medication delivery device comprising: a syringe having a barrel holding a medication and a piston disposed within the barrel, the syringe further including a hollow needle wherein movement of the piston relative to the barrel dispenses medication through the needle, the syringe being movable relative to the medication delivery device between a storage position and a delivery position, wherein the needle projects from the device in the delivery position and is retracted within the device in the storage position; a drive mechanism having a plunger to advance the piston, the drive mechanism including a spring adapted to drive the plunger in a translational movement, move the syringe from the storage position to the delivery position, and advance the piston within the barrel to dispense medication from the syringe in a dispensing event; a retraction mechanism adapted to move the syringe from the delivery position to the storage position in a retraction movement, wherein the retraction mechanism includes a rotary member configured to rotate during the retraction movement; and a sensing system including an accelerometer disposed on the medication delivery device, the accelerometer configured to generate a plurality of first signals indicative of sensed acceleration, an optical sensor disposed on the medication delivery device and positioned to sense rotational movement of the rotary member, the optical sensor configured to generate a plurality of second signals indicative of sensed rotational movement of the rotary member, and a controller operably coupled with the accelerometer and the optical sensor, wherein the controller is configured to determine initiation of the dispensing event based on the plurality of first signals generated by the accelerometer, and configured to determine completion of the dispensing event and completion of the retraction movement based upon the plurality of second signals generated by the optical sensor.

15. The device of aspect 14 wherein the sensor system is configured to record data on each dispensing event based upon the pluralities of first and second signals and communicate the recorded data to a separate device.

16. The device any one of aspects 14-15 wherein the controller is configured to determine a malfunction from at least one of the first signals and the second signals.

17. The device any one of aspects 14-16 wherein an outer circumferential surface of the rotary member includes a plurality of sensor targets recognizable by the optical sensor, wherein the controller is configured to determine from analysis of the plurality of second signals if the medication container was successfully moved from the delivery position to the storage position when the device performs a retraction movement.

18. The device any one of aspects 14-17 wherein the controller is configured to determine the duration of a dispensing event based upon a signal spike from the first signals and an initial spike from the second signals.

19. The device any one of aspects 14-18 wherein the sensor system communicates the initiation of the dispensing event, the completion of the dispensing event and the completion of the retraction movement to a user interface to thereby inform the user of occurrence of the initiation of the dispensing event, the completion of the dispensing event and the completion of the retraction movement.

20. The device of aspect 19 wherein the user interface is disposed on the separate device which receives the recorded data.

21. A method for determining an operational status of a medication delivery device having a needle, a first sensor, a second sensor, a rotary sensor, and a retraction mechanism, comprising: determining an initiation of the dispensing event from a needle in an extended position based on a signal spike of a plurality of first signals generated by a first sensor; determining an end of the dispensing event from said needle in the extended position based on an initial spike of a plurality of second signals generated by a second sensor sensing rotation of a rotary member of a retraction mechanism; determining an end of a needle retraction of said needle from the extended position based upon a predetermined spike of second signals, subsequent to the initial spike of the second signals, generated by the second sensor; and indicating on a user interface at least one of the determined initiation of the dispensing event, the determined completion of the dispensing event, and the determined completion of the needle retraction.

What is claimed is:

1. A medication delivery device comprising:

a housing;

a medication container positioned within the housing and having a container body to hold a medication and a slidable piston operably coupled with the container body, the slidable piston movable relative to the container body to dispense the medication from the medication container, the medication container being movable relative to said housing between a storage position and a delivery position;

an accelerometer embedded on or affixed within the housing and disposed outside of the medication container such that the accelerometer does not directly contact the container body or the slidable piston;

a drive spring adapted to, when a dispensing event is initiated, drive the medication container from the storage position to the delivery position; and a retraction spring adapted to, when a retraction movement is initiated, drive the medication container from the delivery position to the storage position;

wherein the accelerometer is configured to detect a first acceleration caused by motion of the medication container relative to the housing as the medication container is driven from the storage position to the delivery position by the drive spring, and configured to detect a second acceleration caused by motion of the medication container relative to the housing as the medication container is driven from the delivery position to the storage position by the retraction spring; and a controller operably coupled with the accelerometer, wherein the controller is configured to determine an initiation of the dispensing event based on the detected first acceleration, and a completion of the retraction movement based on the detected second acceleration.

2. The medication delivery device of claim 1 further comprising a user interface communicably coupled to the controller, wherein the controller is configured to communicate the initiation of the dispensing event and at least one of a completion of the dispensing event or the completion of the retraction movement to said user interface.

3. The medication delivery device of claim 2, wherein the user interface is disposed on the medication delivery device.

4. The medication delivery device of claim 2, wherein the user interface is separate from the medication delivery device, and the controller is configured to communicate the initiation of the dispensing event and the at least one of the completion of the dispensing event or the completion of the retraction movement wirelessly to the user interface.

5. The medication delivery device of claim 1, wherein the drive spring is adapted to drive the medication container axially in a distal direction, and the retraction spring is adapted to drive the medication container axially in a proximal direction.

6. The medication delivery device of claim 1, further comprising the medication held within the container body.

* * * * *